United States Patent
Delmore et al.

(10) Patent No.: US 6,881,203 B2
(45) Date of Patent: Apr. 19, 2005

(54) MICRONEEDLE ARRAYS AND METHODS OF MANUFACTURING THE SAME

(75) Inventors: Michael D. Delmore, Grant, MN (US); Patrick R. Fleming, Lake Elmo, MN (US); Douglas A. Huntley, Maplewood, MN (US); Jamieson C. Keister, Lakeville, MN (US); Cristina U. Thomas, Woodbury, MN (US); Richard H. Ferber, Fridley, MN (US)

(73) Assignee: 3M Innovative Properties Company, St. Paul, MN (US)

(*) Notice: Subject to any disclaimer, the term of this patent is extended or adjusted under 35 U.S.C. 154(b) by 123 days.

(21) Appl. No.: 09/947,195

(22) Filed: Sep. 5, 2001

(65) Prior Publication Data

US 2003/0045837 A1 Mar. 6, 2003

(51) Int. Cl.[7] .................. A61B 17/20; A61M 37/00; A61M 5/32
(52) U.S. Cl. ........................... 604/272; 604/46
(58) Field of Search .............. 604/20, 22, 272–274, 604/27, 173, 46; 264/400, 225; 163/1

(56) References Cited

U.S. PATENT DOCUMENTS

| 3,964,482 A | 6/1976 | Gerstel et al. |
|---|---|---|
| 4,018,938 A | 4/1977 | Feder et al. |

(Continued)

FOREIGN PATENT DOCUMENTS

| EP | 0407063 | * | 1/1991 |
|---|---|---|---|
| EP | 1 086 718 A1 | | 3/2001 |
| EP | 1 086 719 A1 | | 3/2001 |
| EP | 1 088 642 A1 | | 4/2001 |
| GB | 2 221 394 A | | 2/1990 |
| WO | WO 96/33839 | | 10/1993 |
| WO | WO 94/25259 | | 11/1994 |
| WO | PCT WO 97/03718 | * | 2/1997 .......... A61M/37/00 |
| WO | WO 97/03718 | | 2/1997 |
| WO | WO 99/64580 | | 12/1999 |
| WO | WO 00/05166 | | 2/2000 |
| WO | WO 00/74763 A3 | | 12/2000 |
| WO | WO 00/74763 A2 | | 12/2000 |
| WO | WO 00/74764 A1 | | 12/2000 |
| WO | WO 01/36037 | * | 5/2001 |

OTHER PUBLICATIONS

J. Arnold et al., "Combination of Excimer Laser Micromachining and Replication Processes Suited for Large Scale Production," *Applied Surface Science*, vol.86, pp. 251–258 (1995).

(Continued)

*Primary Examiner*—Nicholas D. Lucchesi
*Assistant Examiner*—Matthew F DeSanto
(74) *Attorney, Agent, or Firm*—Kevin W. Raasch

(57) ABSTRACT

Microneedle arrays, methods of manufacturing microneedles and methods of using microneedle arrays. The microneedles in the microneedle arrays may be in the form of tapered structures that include at least one channel formed in the outside surface of each microneedle. The microneedles may have bases that are elongated in one direction. The channels in microneedles with elongated bases may extend from one of the ends of the elongated bases towards the tips of the microneedles. The channels formed along the sides of the microneedles may optionally be terminated short of the tips of the microneedles. The microneedle arrays may also include conduit structures formed on the surface of the substrate on which the microneedle array is located. The channels in the microneedles may be in fluid communication with the conduit structures. One manner of using microneedle arrays of the present invention is in methods involving the penetration of skin to deliver medicaments or other substances and/or extract blood or tissue.

26 Claims, 7 Drawing Sheets

U.S. PATENT DOCUMENTS

| | | | |
|---|---|---|---|
| 4,165,395 | A | 8/1979 | Chang |
| 4,508,749 | A | 4/1985 | Brannon et al. |
| 4,523,807 | A | 6/1985 | Suzuki |
| 4,568,632 | A | 2/1986 | Blum et al. |
| 4,693,791 | A | 9/1987 | Becker et al. |
| 4,768,358 | A | 9/1988 | Yamazaki et al. |
| 4,822,975 | A | 4/1989 | Torigoe |
| 4,970,366 | A | 11/1990 | Imatou et al. |
| 5,045,439 | A | 9/1991 | Maner et al. |
| 5,055,163 | A | 10/1991 | Bier et al. |
| 5,073,237 | A | 12/1991 | Bacher et al. |
| 5,160,823 | A | 11/1992 | Bennin et al. |
| 5,389,954 | A | 2/1995 | Inaba et al. |
| 5,543,108 | A | 8/1996 | Bacher et al. |
| 6,093,520 | A | 7/2000 | Vladimirsky et al. |
| 6,132,755 | A | 10/2000 | Eicher et al. |
| 6,537,264 | B1 * | 3/2003 | Cormier et al. ............. 604/506 |
| 6,558,361 | B1 * | 5/2003 | Yeshurun ..................... 604/272 |
| 2002/0045859 | A1 * | 4/2002 | Gartstein et al. ........... 604/117 |
| 2002/0133129 | A1 * | 9/2002 | Arias et al. .................. 604/272 |

OTHER PUBLICATIONS

J. Arnold, "Combining Two Technologies for Mass Production: Laser LIGA—Excimer Laser Microstructuring and Replication," *LambdaPhysik, Lambda Highlights* No. 45, pp. 1–3 (Aug. 1994).

J. M. Bartkus et al., "Variable Efficacy of Antiseptics Used as Patient Preoperative Skin Preparations," 3M Medical Markets Online Information System [online](1997) [retrieved on Dec. 14, 2001]. Retrieved from the Internet: <URL:http:// mmglab1.mmm.com/MMGAsepsis/preop_products/duraprep/efficacy_studies/Variable Efficacy/Variable Efficacy.htm>. 3 pages total.

J. E. Bischoff, "Finite Element Modeling of Human Skin Using an Isotrope, Nonlinear Elastic Constitutive Model," *Journal of Biomechanics*, vol. 33, No. 6, pp. 645–652 (2000).

B. Braren et al., "Optical and Photochemical Factors Which Influence Etching of Polymers by Ablative Photodecomposition," *Journal of Vacuum Science Technology*, B3(3), pp. 913–917 (May/Jun. 1998).

T. Hodapp et al., "Modeling Topology Formation During Laser Ablation," *Journal of Applied Physics*, vol. 84, No. 1, pp. 577–583 (Jul. 1, 1998).

S. A. Malcolm, "The Demonstration of Bacteria On and Within the Stratum Corneum Using Scanning Electron Microscopy," *British Journal of Dermatology*, vol. 102, pp. 267–275 (1980).

* cited by examiner

100
MICRONEEDLE ARRAYS AND METHODS OF MANUFACTURING THE SAME

The present invention relates to the field of microneedle arrays.

BACKGROUND

Arrays of relatively small structures, sometimes referred to as microneedles or micro-pins, have been disclosed for use in connection with the delivery and/or removal of therapeutic agents and other substances through the skin and other surfaces.

The vast majority of known microneedle arrays include structures having a capillary or passageway formed through the needle. Because the needles are themselves small, the passageways formed in the needles must be limited in size. As a result, the passageways can be difficult to manufacture because of their small size and the need for accurate location of the passageways within the needles.

Another potential problem of passageways small enough to fit within the microneedles is that the passageways may become easily obstructed or clogged during use.

As a result, a need exists for microneedle arrays that include fluid passageways that are easier to manufacture and that are resistant to obstruction or clogging during use.

Among the uses for microneedle arrays, penetration of skin is one commonly-discussed application. Skin is a three-layer protective barrier between the body and the outside world. At approximately 200 um thick, the epidermis is the thinnest, outermost layer of the skin and it contains many of the components that give skin it barrier-like characteristics. The outermost layer of the epidermis, the stratum corneum, is a thin layer (10–50 um) of flattened, dead cells, water, and lipids that helps the body retain water and prohibits the entrance of microorganisms and toxic chemicals. The stratum corneum, sometimes called the "horny layer" is both tough and flexible, with a significant degree of elasticity. These characteristics make the stratum corneum an effective barrier, resistant to penetration. There is significant variability in the thickness and elasticity of the stratum corneum associated with age and location on the body. For example, the stratum corneum of the feet is over ten times thicker than that found on the forearm of a typical human.

Beneath the epidermis is the dermis which houses blood vessels and nerve endings, hair shafts and sweat glands. Thousands of small capillaries (loop capillaries) feed the upper levels of the dermis, beneath the epidermis. These capillaries extend just above most of the nerve endings that also reside in the dermis. The deepest layer of skin, the hypodermis, insulates the body from extreme temperatures and provides a mechanical cushion from outside assaults. The hypodermis contains larger blood vessels and arteries and more nerves.

Delivery of substances into the skin or removal of fluids through the skin may be facilitated by the use of microneedle arrays. One problem associated with penetration of skin by microneedle arrays is, however, the viscoelastic properties of skin. When subjected to static or slow-moving loads, skin elongates before rupture.

As a result, many situations requiring the extraction of fluids, e.g., blood-glucose monitoring, required the use of sharp instruments such as lancets that pierce the skin. Such devices are, however, relatively painful to use and may pose a risk of inadvertent piercing of skin. Further, the pierced site may experience unnecessary bleeding.

SUMMARY OF THE INVENTION

The present invention provides microneedle arrays, methods of manufacturing molds for microneedle arrays, and methods of manufacturing microneedles from the molds. The microneedles in the microneedle arrays are tapered structures that include at least one channel formed in the outside surface of each microneedle. The channels may assist in the delivery or removal of fluids using the microneedle arrays.

In some embodiments, the microneedles include bases that are elongated in one direction. Such a configuration may provide microneedles with improved rigidity and structural integrity as compared to microneedles that do not include elongated bases. Further, the channels in microneedles with elongated bases may extend from one of the ends of the elongated bases towards the tips of the microneedles. That configuration may also provide channeled microneedles with improved rigidity and structural integrity as compared to channeled microneedles that do not include elongated bases.

In other embodiments, the channels formed along the sides of the microneedles may optionally be terminated short of the tips of the microneedles to improve the structural integrity of the tips and potentially improve their piercing ability.

The microneedle arrays of the present invention may also include conduit structures formed on the surface of the substrate on which the microneedle array is located. The channels in the microneedles may preferably be in fluid communication with the conduit structures to potentially assist with the delivery or removal of fluids through the channels. The conduits may be formed as depressions or grooves in the substrate surface or they may be formed by barriers, similar to dikes, that protrude above the substrate surface.

The microneedle arrays of the invention may be used in a variety of different manners. One manner of using microneedle arrays of the present invention is in methods involving the penetration of skin to deliver medicaments or other substances and/or extract blood or tissue. As discussed above, it may be desired that the height of the microneedles in the microneedle arrays be sufficient to penetrate the stratum corneum.

In addition to having a sufficient length, it may be preferred to provide the microneedle arrays in combination with devices that are capable of delivering the microneedle arrays to the skin in a manner that results in effective piercing of the stratum corneum. To do so, it may be preferred to apply a brief impact force to the microneedle array such that the microneedles on the array are rapidly driven into the stratum corneum.

It should be understood that impact delivery of microneedle arrays as discussed herein may not necessarily be limited to microneedle arrays that include microneedles with channels as described in connection with FIGS. 1–4. The impact delivery devices and methods described herein may be used with many different microneedle arrays.

In one aspect, the present invention provides a microneedle device that includes a plurality of microneedles projecting from a substrate surface, wherein each of the microneedles has a tapered shape with an outer surface, a base proximate the substrate surface, and a tip distal from the base, and further wherein the base is elongated along an elongation axis on the substrate surface such that the base has opposing ends along the elongation axis. Each microneedle also includes a channel formed in the outer surface of each microneedle of the plurality of microneedles, each channel extending from the base towards the tip of the microneedle.

In another aspect, the present invention provides a microneedle device that includes a plurality of microneedles projecting from a substrate surface, wherein each of the microneedles has a tapered shape with an outer surface, a base proximate the substrate surface and a tip distal from the base. Each of the microneedles also includes a channel formed in the outer surface of each microneedle of the plurality of microneedles, each channel extending from the base of the microneedle towards the tip of the microneedle, wherein the channel terminates short of the tip of the microneedle.

In another aspect, the present invention provides a method of delivering a microneedle array to a skin impact site by positioning a microneedle array proximate a delivery site, the microneedle array including a plurality of microneedles protruding from a surface; and applying an impact force to the microneedle array over a period of less than about 1 second, wherein the plurality of microneedles are driven through the stratum corneum at the skin impact site.

In another aspect, the present invention provides a microneedle array delivery device that includes a microneedle array having a plurality of microneedles protruding from a surface; a driver operably connected to the microneedle array, wherein the driver has stored energy; wherein release of the stored energy results in application of an impact force to the microneedle array over a period of less than about 1 second.

These and other features and advantages of the invention may be described below in connection with various illustrative embodiments of the invention.

DETAILED DESCRIPTION OF THE ILLUSTRATIVE EMBODIMENTS OF THE INVENTION

Figure 1:
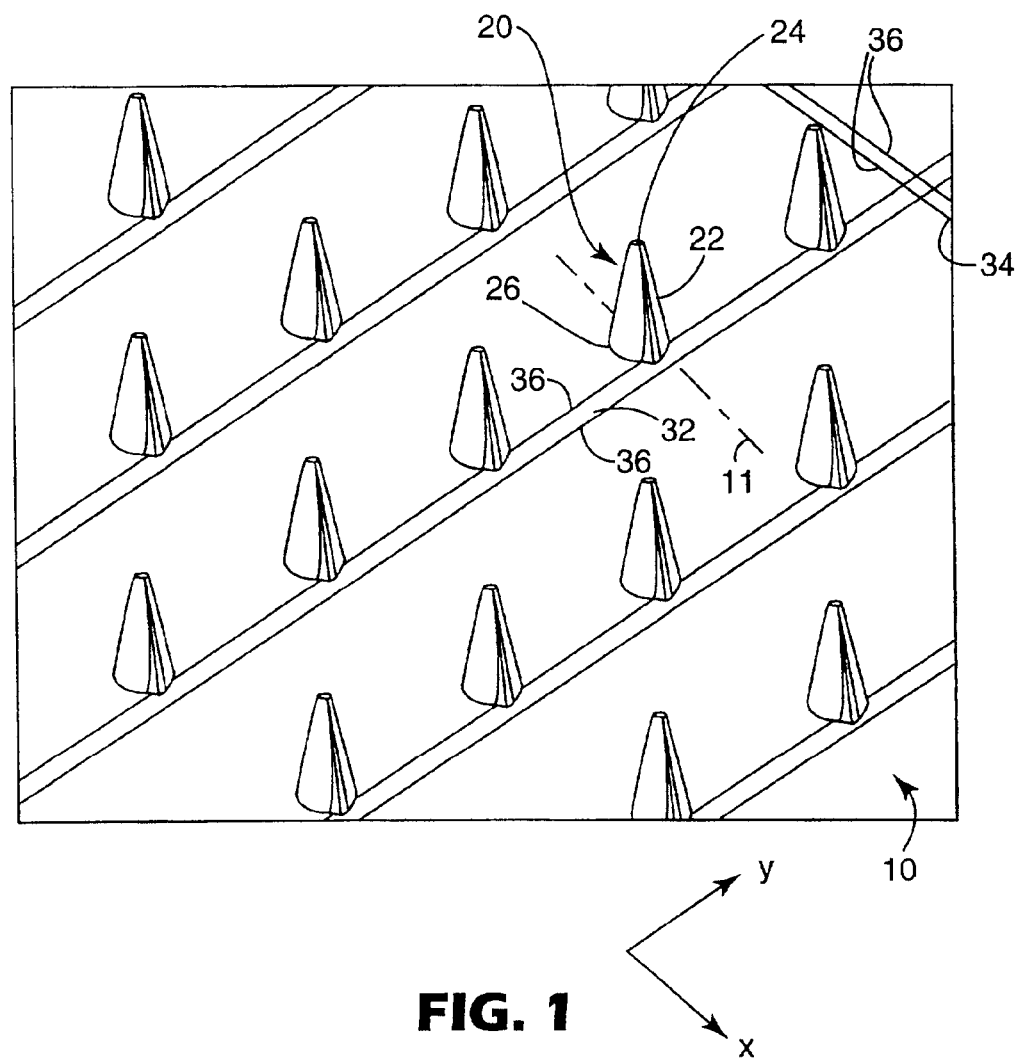
FIG. 1 is a perspective view of one microneedle array according to the present invention.

The present invention provides a microneedle array that may be useful for a variety of purposes. For example, the microneedles may be used to deliver or remove fluids from the point at which they are inserted. To accomplish that goal, the microneedles include a channel formed in the outer surface of a tapered structure. The channel extends from a base or near a base of the microneedle towards the tip of the microneedle. The channel is typically formed as a void running along the side of the microneedle. In some embodiments, the channel may extend to the tip of the microneedle and, in other embodiments, the channel may terminate before reaching the tip.

The channels formed in microneedles of the present invention can be distinguished from bores or vias formed in known microneedles because they are open along substantially their entire length, e.g., from the base of the microneedle to the terminus of the channel. In contrast, bores or vias formed in known microneedles typically are closed fluid pathways that have an opening at the tip of the needle structure.

In some embodiments, the bases of the microneedles may be elongated to improve the rigidity and structural integrity of the microneedles. In the microneedles with bases that are elongated along an elongation axis, it may be preferred that the channels extend from one of the opposing ends located along the elongation axis.

Additional features that may be included in the microneedle arrays of the present invention are conduit structures in fluid communication with the channels formed in the microneedles. The conduit structure may be used to deliver fluids to the channels in the microneedles or they may be used to remove fluids from the channels of the microneedles. In some situations, the conduits and channels may both deliver and remove fluids from microneedle insertion sites.

The microneedle arrays of the present invention may be used for a variety of purposes. For example, the microneedles may be used to deliver drugs or other pharmacological agents through the skin in a variation on transdermal delivery. Where the microneedles are to be used for transdermal drug delivery, the height of the microneedles is preferably sufficient to pass through the stratum corneum and into the epidermis. It is also, however, preferable that the height of the microneedles is not sufficiently large to reach the dermis, thereby avoiding contact with nerves and the corresponding potential for causing pain.

In addition to transdermal drug delivery, the microneedle arrays of the present invention may also find use as a mechanical attachment mechanism useful for attaching the microneedles arrays to a variety of surfaces. For example, the microneedle arrays may be used to affix a tape or other medical device to, e.g., the skin of a patient.

As used in connection with the present invention, the term "microneedle" (and variations thereof) refers to structures having a height above the surface from which they protrude of about 500 micrometers or less. In some instances, microneedles of the present invention may have a height of about 250 micrometers or less.

Referring now to FIG. 1, a portion of one array of microneedles 20 is illustrated as arranged in rows extending in the y direction on the surface 12 of a substrate 10. The microneedles 20 may preferably be arranged in successive rows that are, in the depicted embodiment, uniformly spaced apart in the x direction. The microneedles 20 each include a channel 22 formed in the outer surface of the tapered microneedle.

Each of the channels 22 may be in fluid communication with an optional conduit structure formed on the substrate surface 12 along each row of microneedles 20. The conduit structures include branch arteries 32 in direct communication with the channels 22, and the branch arteries 32 are in fluid communication with each other through at least one main artery 34 of the conduit structures as depicted in FIG. 1.

The conduit structure may be formed in any suitable manner that defines fluid pathways on the substrate surface 12. The conduit structure may, for example, be formed using barriers 36 that project from the substrate surface 12. One alternative for forming conduit structure is to form depressions or grooves into the substrate surface 12. In some instances, the conduit structure may be formed by any suitable combination of protruding barriers and depressions. In other instances, the conduit structure may, in fact, include no structure, but rather be provided in the form of a pattern of low surface energy on the substrate surface 12. The low surface energy may be provided by, e.g., coatings, surface treatments, etc.

Figure 2:
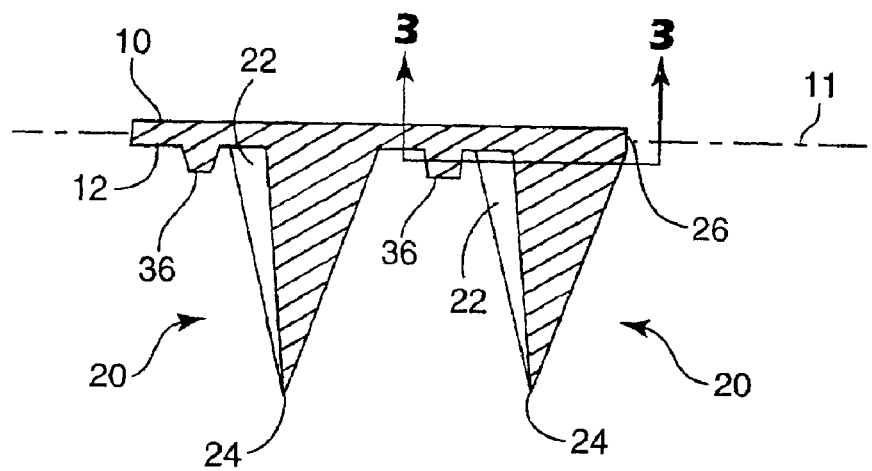
FIG. 2 is a partial cross-sectional view of two microneedles in a microneedle array according to the present invention.
Figure 3:
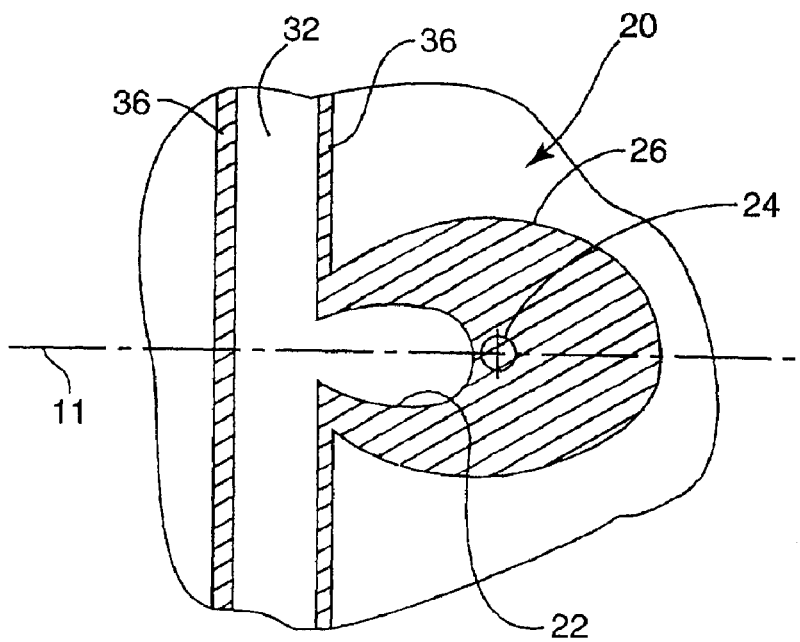
FIG. 3 is an enlarged cross-sectional view of one microneedle of FIG. 2 taken along line 3—3 in FIG. 2.

Referring to FIGS. 1, 2 and 3, each of the microneedles 20 includes a base 26 on the substrate surface 12, with the microneedle terminating above the substrate surface in a tip 24. The base 26 may be formed in any suitable shape, although in some embodiments the base 26 may have a shape that is elongated along an elongation axis 11 on the substrate surface 12 as seen, e.g., in FIG. 2. The elongated base 26 includes two opposing ends located opposite from each other along the elongation axis 11. By providing microneedles 20 with an elongated base 26, the microneedles 20 may exhibit improved rigidity and/or structural integrity during use, particularly when subjected to forces aligned along the elongation axis 11.

In the depicted embodiment, the channel 22 is located in one of the opposing ends of the microneedle 20, where the opposing ends are located on opposing sides of the base 26 along the elongation axis 11. Such a construction may enhance the ability of the microneedle 20 to withstand shearing forces along the substrate surface 12 in the elongated direction of the base 26.

Although the elongated microneedle base 26 illustrated in FIG. 3 is oval in shape, it will be understood that the shape of the microneedles 20 and their associated bases 26 may vary with some bases, e.g., being elongated along one or more directions and others being symmetrical in all directions.

Figure 2A:
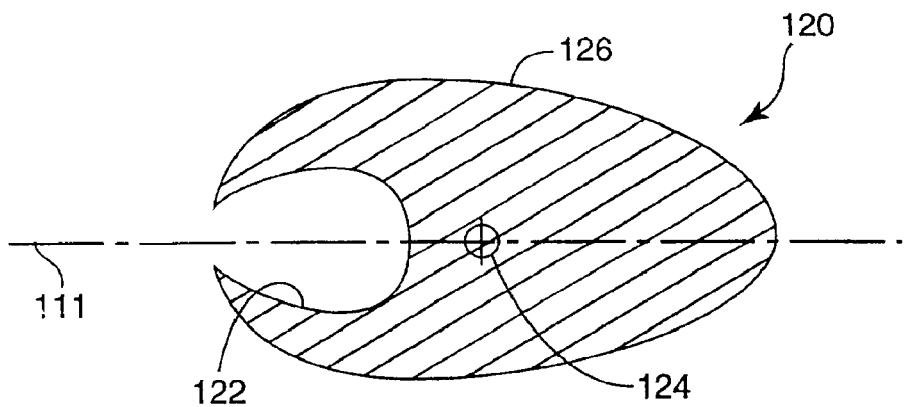
FIGS. 2A–2C are cross-sectional views of microneedles with differently shaped bases according to the present invention.

For example, FIG. 2A depicts an alternative microneedle 120 with a egg-shaped base 126 defining an axis of elongation 111 that is aligned between opposing ends of the elongated base 126. A channel 122 extends from the base 126 towards the tip 124 of the microneedle 120. It should be understood that the tip 124 is only an illustration of the location of the tip projected onto the base of the microneedle 120.

Figure 2B:
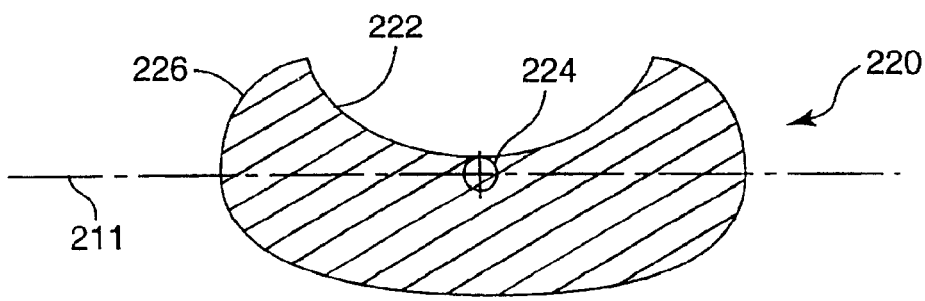

FIG. 2B depicts another microneedle 220 having a tip 224 (again, a projection of the tip) and an oval-shaped base 226 in which the channel 222 is located at an intermediate location between the opposing ends of the base 226 (as defined by the elongation axis 211). This embodiment depicts a microneedle in which the channel 222 is not located in one of the opposing ends of the microneedle 220, rather, the channel 222 is located intermediate, i.e., between the opposing ends of the base 226.

Figure 2C:
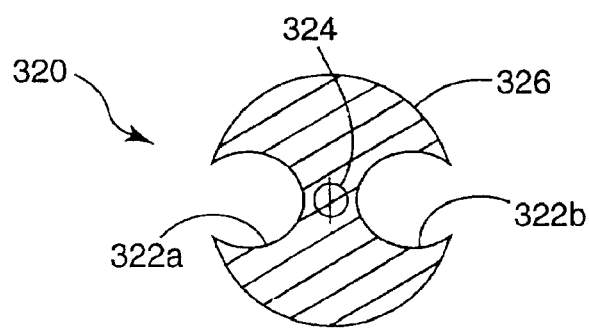

FIG. 2C depicts another microneedle 320 according to the present invention in which the microneedle 320 has a tip 324 (again, a projection of the tip) and a circular base 326 with two channels 322a and 322b formed in the microneedle 320. Microneedles of the present invention may include only one channel (as depicted in, e.g., FIGS. 1, 2, 2A, and 3B) or they may include more than one channel as depicted in FIG. 2C.

The general shape of the microneedles of the present invention is tapered. For example, the microneedles 20 have a larger base 26 at the substrate surface 12 and extend away from the substrate surface 12, tapering at a tip 24. It may be preferred, e.g., that the shape of the microneedles be generally conical.

Figure 2D:
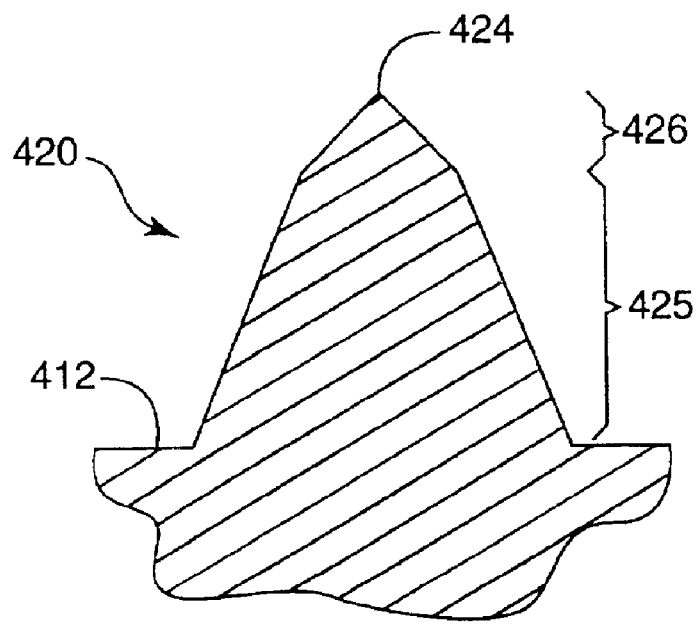
FIGS. 2D and 2E are cross-sectional views of alternative microneedles.

Although the microneedles depicted in FIG. 2 have a uniform slope or wall angle (with respect to, e.g., a z axis normal to the substrate surface 12), microneedles of the present invention may have different wall angles. For example, FIG. 2D is a cross-sectional view of one microneedle 420 including a lower section 425 having steeper wall angles with respect to the substrate surface 412, and an upper section 426 having shallower wall angles proximate the tip 424 of the microneedle 420.

Figure 2E:
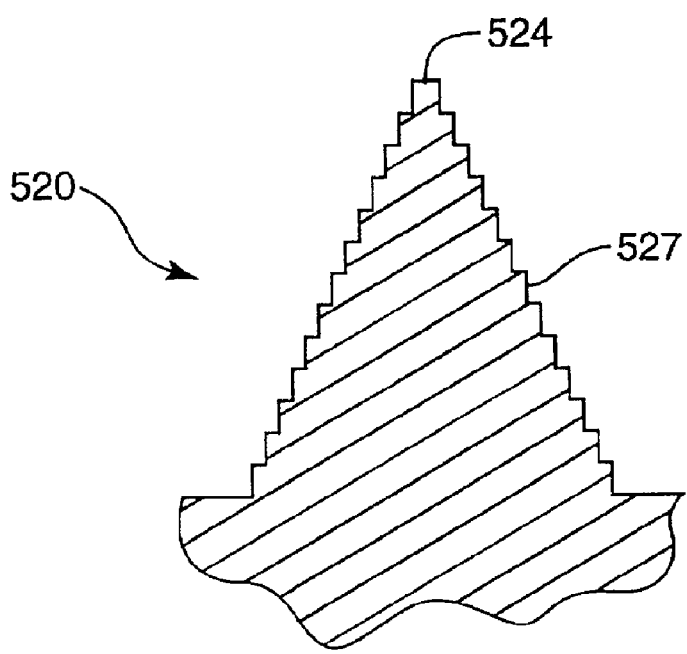

Another variation, depicted in FIG. 2E, is that the surface of the microneedles of the present invention need not necessarily be smooth. The sidewalls 527 of the microneedles 520 may, instead, be stepped as seen in FIG. 2E as the sidewalls move from the substrate surface 512 to the tip 524 of the microneedle 520.

One manner in which the microneedles of the present invention may be characterized is by height. The height of the microneedles 20 may be measured from the substrate surface 12 or from the top surface of the barriers 32 forming conduits 30. It may be preferred, for example, that the base-to-tip height of the microneedles 20 be about 500 micrometers or less as measured from the substrate surface 12. Alternatively, it may be preferred that the height of the microneedles 20 the about 250 micrometers or less as measured from the base 26 into the tip 24.

Other potentially preferred dimensions for the microneedles 20 may be discussed with reference to FIG. 3. It may be preferred that the largest dimension of the base 26 of microneedles 20 with an elongated oval base be approximately 100 micrometers or less, while the shorter dimension of the base 26 of microneedle 20 be about 65 micrometers or less. These dimensions apply to microneedles with a base to tip height of approximately 220 micrometers.

Some exemplary dimensions for the channel 22 of microneedles 20 may also be described with reference to FIGS. 2 and 3. These dimensions are provided as examples only, and are not intended to limit the scope of the invention unless explicitly recited in the claims. The width of the channel 22 (as measured along the shorter dimension of the base 26) may, for example, be about 3 to about 40 micrometers.

Further, although the channels associated with microneedles of the present invention are depicted as having relatively smooth surfaces (see, e.g., FIGS. 2, 3, 2A–2C), the channels may preferably have a surface that is not smooth, e.g., the surfaces of the channels may be roughened, structured, etc. to enhance fluid flow.

Another manner in which microneedles having an elongated base may be characterized is in the relationship between the dimensions of the base and the channel. Referring to FIG. 3, it may be preferred that the channel 22 have a channel depth measured along the elongation axis 11 at the base of the microneedle 20 that is less than half of the dimension of the base 26 of the microneedle 20 as measured along the elongation axis 11.

The length of the channel 22 along microneedles 20 may also a vary. It may, for example, be preferred that the height of the channel 22, i.e., its length from the base 26 to the point at which the channel 22 terminates, may preferably be less than the base to tip height of the microneedle 20. By terminating the channel 22 short of the microneedle tip 24, the integrity of the tip 24 may be better maintained. In addition, the tip 24 of the microneedle 20 may be sharper, thereby potentially improving the ability of the microneedle 20 to pierce a surface or material against which it is pressed.

The microneedles 20 are each depicted with one channel 22 formed along a side the thereof. It should, however, be understood that microneedles of the present invention may be formed with more than one channel as discussed above. It will, also be understood that in such circumstances, the size of the channels may be reduced relative to the overall size of the microneedles to improve the structural characteristics of the microneedle.

Figure 4:
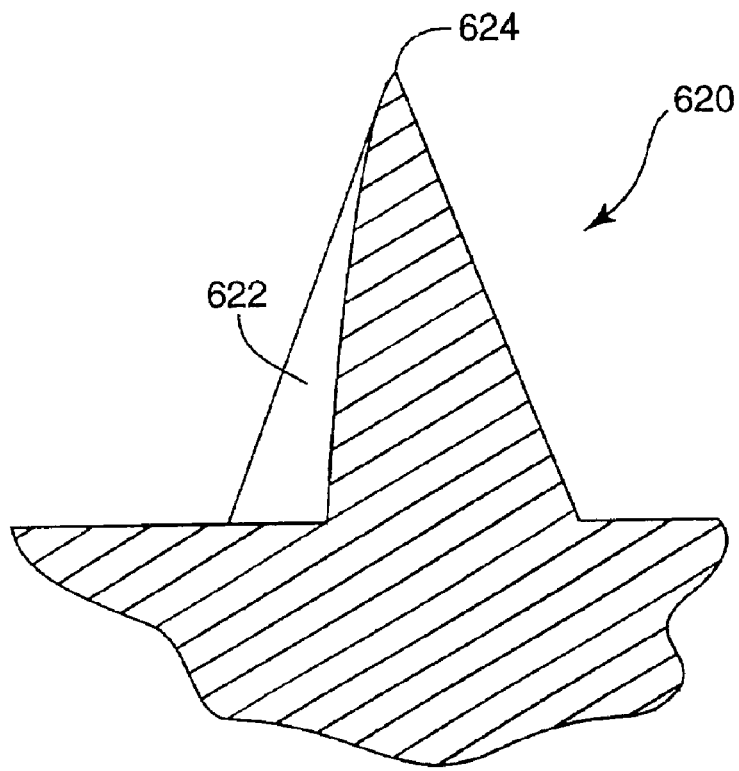
FIG. 4 is a cross-sectional view of a microneedle including a channel that terminates short of the tip of the microneedle.

In addition to (or in place of) elongating the base of the microneedles to improve their structural characteristics, that channel or channels provided in the microneedles may be terminated short of the tip of the microneedle. Doing so may improve the structural characteristics of the microneedles and/or may also improve the sharpness or penetration characteristics of the microneedles. Referring to FIG. 4, one example of a microneedle 620 is depicted in cross-section.

The microneedle 620 includes a channel 622 that terminated short of the tip 624 of the microneedle 620. Although only one channel is depicted in the microneedle 620 of FIG. 4, it will be understood that more than one channel could be provided.

Returning to FIG. 2, two of the barriers 36 used to form conduit structure as seen in FIG. 1 are depicted in cross-section. The barriers 36 are provided in the form of projections from the substrate surface 12 similar to the microneedles 20. The barriers 36 that form the opposite sides of the branch arteries 32 of the conduit structure are not depicted in FIG. 2 because they are either outside the depicted view (on the left side) or hidden behind the left-most microneedle.

As with the microneedles 20, the dimensions associated with the barriers and conduit structure formed by the barriers 36 may vary depending on the applications for which the microneedle arrays are intended. For example, it may be preferred that the distance between barriers 36 forming one of the branch arteries 32 in direct fluid communication with the channels 22 in the microneedles be spaced apart from each other by a distance that is equivalent to or less than the smallest dimension of the channel 22 at the base 26 of the microneedle 20 as seen in, e.g., FIG. 3. In channel 22 of FIG. 3, the smallest dimension of the channel 22 is transverse to the axis 11.

By providing barriers 36 with that spacing, capillary action between the channels 22 and the branch arteries 32 may be enhanced. Such a relationship is depicted in, e.g. FIG. 3, where the distance between the barriers 36 along axis 11 that form the branch artery 32 is less than the depth of the channel 22 along the axis 11.

In another manner of characterizing the barriers 36, it may be preferred that the height of the barriers 36 above the substrate surface 12 be selected such that the barriers 36 do not interfere with penetration of a surface by the microneedles 20. In other words, the barrier height should not prevent the microneedles from reaching a desired depth.

A potential advantage of the barriers 36 forming the conduit structures is that the barriers 36 may provide a sealing function when the array is in position against, e.g., the skin of a patient. By sealing the fluid paths into and/or out of the channels in the microneedles 20, additional control over fluid flow within the array may be achieved.

The microneedles 20 and conduit structure may preferably be manufactured integrally with the substrate 10. In other words, the microneedles 20, conduit structure 30, and substrate 10 are preferably formed as a one piece, completely integral unit. Alternatively, the microneedles and/or conduit structures may be provided separately from the substrate 10.

The microneedle arrays may be manufactured from a variety of materials. Material selection may be based on a variety of factors including the ability of the material to accurately reproduce the desired pattern; the strength and toughness of the material when formed into the microneedles; the compatibility of the material with, for example, human or animal skin; the compatibility of the materials with any fluids to be delivered or removed by the channels formed in the microneedles, etc. For example, it may be preferred that the microneedle arrays of the present invention be manufactured of one or more metals.

Regardless of the materials used for the microneedle arrays of the present invention, it may be preferred that the surfaces of the microneedle array that are likely to come into contact with fluids during use have certain wettability characteristics. It may be preferred that these surfaces are hydrophilic, e.g., exhibit a static contact angle for water of less than 90 degrees (possibly less than about 40 degrees), so that the fluid can be spontaneously wicked via capillary pressure. The hydrophilic nature of the surfaces may be provided by selection of materials used to manufacture the entire microneedle array, surface treatments of the entire array or only those portions likely to come into contact with fluids, coatings on the entire array or only those portions likely to come into contact with fluids, etc.

Microneedles in the microneedle arrays of the present invention can be solid or porous. As used herein, the term "porous" (and variations thereof) means having that the microneedles include pores or voids through at least a portion of the structure, wherein those pores or voids are sufficiently large and interconnected to permit at least fluid passage.

Figure 5:
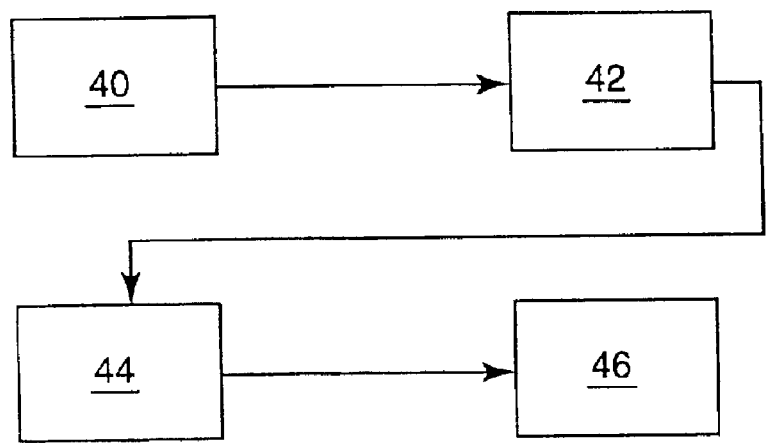
FIG. 5 is a diagram of one process for manufacturing microneedle arrays according to the present invention.

One preferred process for forming microneedle arrays according to the present invention is illustrated in FIG. 5. Briefly, the method involves providing a substrate 40, forming a structured surface in the substrate 42, the structured surface including cavities having the shape of the desired microneedles and any other features (e.g., barriers for the conduits). A metallic microneedle array can then be electroformed on the structured surface 44, followed by separation of the structured surface from the metallic microneedle array 46.

FIG. 5 illustrates the formation of a structured surface in a substrate as the initial activity. Although the preferred method of manufacturing microneedle arrays according to the present invention involves laser ablation of a mold substrate (using, e.g., an excimer laser) to provide cavities in the shape of the desired microneedles, it should be understood that any suitable method of forming cavities in the desired shape may be substituted for the method described herein. For example, the cavities may be formed by conventional photolithography, chemical etching, ion beam etching etc. The preferred laser ablation lithography techniques constitute only one method of forming the desired microneedles arrays.

The process of forming the structured surface begins with a substrate having sufficient thickness to allow the formation of a structured surface having needle cavities of the desired depth. The depth of the needle cavities controls the height of the microneedles. As a result, the substrate used to form the structured surface must have a thickness that is at least equal to or greater than the desired height of the microneedles. Preferably, the substrate used to form the structured surface has a thickness that is greater than the desired height of the microneedles.

Examples of suitable materials for mold substrates used in connection with the present invention include, but are not limited to, polyimide, polyester, polyurethane epoxy, polystyrene, polymethylmethacrylate, and polycarbonate. Regardless of the exact material or materials, it may be preferred that the mold substrate be free of any inorganic fillers, e.g., silica, iron fibers, calcium carbonate, etc. One preferred mold substrate material is a polyimide, e.g., KAPTON H or KAPTON E from DuPont (Wilmington, Del.), because of its ablation properties when exposed to energy from excimer lasers.

In the case of films that are not thick enough to serve as a mold substrate, two or more of the films may be laminated together to provide a mold substrate of suitable thickness. If a bonding agent (e.g., an adhesive) is used to laminate two films together, it may be preferred that the bonding agent possess optical and/or ablation properties similar to the films. Those material properties may include, for example, energy absorption coefficient at a selected wavelength, a uniform index of refraction; a low level of crystallinity; etc. In addition, it may be preferred that the bonding agent be free of inorganic components, e.g., silica, iron fibers, calcium carbonate, etc.

The laminated substrate preferably contains no voids between films and possesses good interlayer adhesion. As a result, it may be preferred to laminate the films at elevated temperatures, under some pressure, and/or in a vacuum. Further, it may be desirable to treat the surface of one or more of the films to promote adhesion and to limit void formation. One example of a potentially desirable treatment is plasma etching, although many other surface treatments may be used in place of, or in addition to, plasma etching.

One potentially preferred method of preparing a laminated polyimide substrate includes laminating two polyimide films using an epoxy (e.g., PR-500 available from Minnesota Mining and Manufacturing Company, St. Paul, Minn.). Prior to application of the epoxy, the surfaces of the films are plasma etched. The epoxy may preferably be coated in a solvent solution to, e.g., enhance uniformity of the epoxy layer after evaporation of the solvent. Following drying of the epoxy/solvent solution, the films are laminated together under heat and pressure, preferably in a subatmospheric pressure environment. The temperature at which the lamination is carried out is preferably high enough to melt the epoxy (i.e., at or above the $T_m$ of the epoxy), thereby enhancing bubble removal and uniform thickness of the epoxy layer.

After a substrate of sufficient thickness has been obtained (through lamination or otherwise), it may be desirable to laminate the substrate to a base layer to support the substrate during laser ablation or other techniques used to form the structured surface. The base layer preferably maintains the substrate in a substantially planar configuration during processing to hold the substrate within, e.g., the object plane of the laser ablation system during ablation. The base layer may, for example, be glass or any other suitable material. It may further be preferred that the surface of the base layer to which the substrate is laminated have a flatness on the order of 10 micrometers. The substrate may be laminated to the base layer using any suitable technique including, but not limited to, adhesives, curable resins, etc.

After the substrate is attached to the base layer, it is processed to form a structured surface including needle cavities in the shape of the desired microneedles. As discussed above, one preferred process of forming the cavities is laser ablation using a mask. A method of using such mask in connection with laser energy will be described below, although it should be understood that, unless otherwise indicated, preparation of the structured surface is not to be limited to the use of laser energy.

Figure 6:
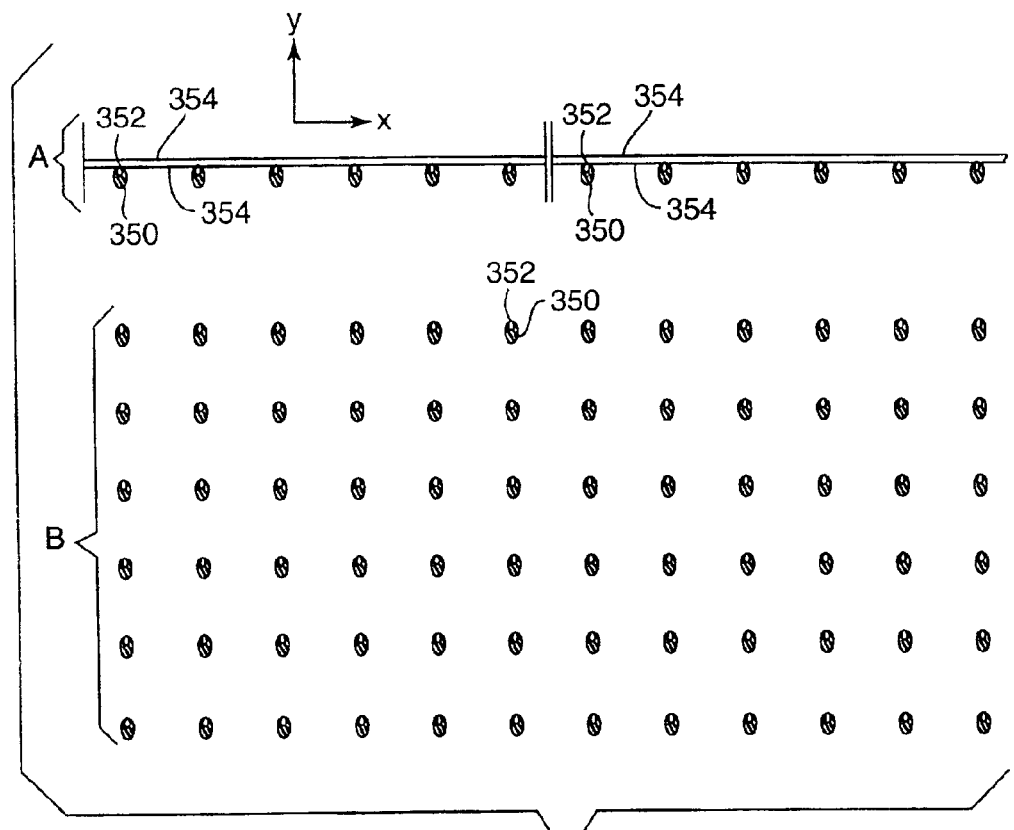
FIG. 6 illustrates one mask useful in manufacturing a microneedle array according to the present invention.

One example of a mask pattern useful for forming a structured surface for the eventual production of an array of microneedles with channels and conduits in fluid communication with the channels is depicted in FIG. 6. The mask pattern includes one row of needle apertures 350 aligned in the x direction as seen in FIG. 6. The row of needle apertures 350 is interconnected by one set of barrier apertures 354 corresponding to the barriers in the conduit structures. The barrier apertures 354 extend in both the x and y directions, i.e., along the row of needle apertures 350 and in the y direction at the ends of the barrier apertures. The portions of the barrier apertures 354 that extend in the y direction are used to form the barriers of the main arteries (see, e.g., FIG. 1).

In addition, each of the needle apertures 350 includes a channel feature 352 corresponding to the desired location of the channel on the microneedle corresponding to the needle aperture.

The mask itself may, e.g., be manufactured using standard semiconductor lithography mask techniques. The patterned portions of the mask are opaque to the laser energy used to pattern the substrate, e.g., ultraviolet light in the case of excimer laser energy. The mask may include a support substrate that is transparent to the laser energy. For example, the patterned portions may be formed of aluminum while the support substrate is fused silica. One alternative for the aluminum may be a dielectric stack that is opaque for light of the desired wavelengths.

The needle apertures 350 in the mask are preferably arranged in successive rows that are uniformly spaced apart (along the x axis). It is further preferred that the spacing between the needle apertures along the rows are also uniform (along the y axis). With uniform spacing between the needle apertures and associated conduit apertures, laser ablation processes similar in many respects to those described in International Publication No. WO 96/33839 (Fleming et al.) and its U.S. priority applications, can be used to form cavities in the substrate.

One of the ways in which the preferred laser ablation process differs from that disclosed in WO 96/33839 is that a telecentric imaging system is used to deliver laser energy to the mask. The telecentric imaging system provides principal rays that are parallel to the optical axis. As a result, the image does not change size when out of focus. In addition, projected features at the center of the mask are the same size as those found at the edges of the mask.

By providing both the needle apertures and the barrier apertures in the same mask, the present invention provides a number of advantages. Among those advantages is the ability to provide microneedles and the associated conduit structures in registration with each other because the features can be imaged at the same time. This can be particularly important in producing devices such as microneedle arrays in which the features are spaced apart in distances measured in micrometers.

Control over the depth of the different cavities formed in the substrate (corresponding to the different heights of the microneedles and barriers on the microneedle arrays) can be obtained by, e.g., selectively covering or masking the different features on the mask while ablating the underlying substrate through the apertures that are not covered or masked. That process can be used, e.g., to obtain barrier cavities that are shallower than the microneedle cavities.

Use of the mask pattern depicted in FIG. 6, for example, may proceed with a first exposure of the substrate located beneath portion A of the mask pattern, i.e., the row of needle apertures 350 interconnected by the barrier apertures 354. As a result, the substrate is exposed during the first exposure in a pattern corresponding to portion A of the mask pattern.

Movement of the mask pattern and the substrate being exposed relative to each other in the y direction can then be used to align the mask apertures 350 in the uppermost row of portion B with the parts of the substrate exposed by the needle apertures 350 in portion A during the first exposure. A second exposure then results in another exposure through the needle apertures to ablate more of the substrate, thereby increasing the depth of the needle cavities in the substrate without also increasing the depth of the barrier cavities. Step-wise movement and exposure can then be repeated until the needle cavities and the barrier cavities are formed to the desired depth in the substrate.

Control over the wall angles of the needle cavities may be achieved by any suitable technique or combination of techniques. Examples of suitable techniques may be described in, e.g., T. Hodapp et el., "Modeling Topology Formation During Laser Ablation," J. Appl. Physics, Vol. 84, No. 1, pp. 577–583 (Jul. 1, 1998).

When processing a polyimide mold substrate through laser ablation, it may be preferred that the mold substrate be located in an oxygen atmosphere to improve subsequent plating of the cavities thus formed.

After completion of the structured surface, the substrate provides a negative of the desired microneedle array structure, with needle cavities corresponding to the shape of the microneedles and conduit cavities corresponding to the desired shape of the conduit structures. As for the needle cavities, they are preferably generally tapered in shape, with a channel structure extending into the tapered shape of the needle cavity.

The resulting mold substrate is then preferably electroplated to form a metallic positive of the microneedle array. Before electroplating, however, the substrate may preferably be cleaned to remove any debris that is, e.g., associated with the laser ablation processing used to form the negative image in the substrate. One suitable cleaning process may include locating the substrate in an ultrasonic bath of detergent and water, followed by drying.

After cleaning the mold substrate, a seed layer of one or more conductive metals is preferably first deposited to provide a conductive surface, followed by heavier electroplating in, e.g., a nickel bath. The seed layer may be deposited by sputtering, chemical vapor deposition, a silver bath, or any other suitable method. To enhance proper filling of the cavities and fidelity of the resulting microneedles to the shape of the cavities, it may be preferred that the seeding be continued until a thicker seed layer is deposited. For example, it may be preferred that the seed layer be deposited with a thickness of about 0.5 micrometers or more, possibly even about 1 micrometer.

Following formation of the seed layer, the seeded mold substrate can then be electroformed with a thicker layer of, e.g., nickel, to form a metallic microneedle array. After filling the cavities in the mold substrate, the plating process is preferably continued until a backplate is formed on the mold substrate with a thickness sufficient to support the microneedle array. For example, a backplate with a thickness of about 0.5 millimeters to about 3 millimeters or more may be formed. If desired, the surface of the backplate opposite the microneedle structures may be polished. That polishing may preferably be carried out while the substrate is still attached to a base layer as described above.

After the metallic microneedle array is formed, the mold substrate can be removed from the microneedle array by any suitable technique or combination of techniques. Some suitable techniques include, but are not limited to, chemical etching, shock freezing, laser ablation, etc. For example, a polyimide substrate may be removed from a microneedle array using an etchant, e.g., potassium hydroxide (KOH).

Because the needle cavities in the structured surface may have a relatively high aspect ratio, it may be desirable to use an electroplating process capable of accurately filling the high aspect ratio cavities. For example, it may be desirable to carry out the electroplating process in the presence of ultrasonic energy for at least a portion of the electroplating. Examples of some suitable systems for and processes of electroplating in the presence of ultrasonic energy may be described in e.g., U.S. patent application Ser. No. 09/946,922, filed on even date herewith, and titled ULTRASONICALLY-ENHANCED ELECTROPLATING SYSTEMS AND METHODS by H. Zhang, et al.

The microneedle arrays of the invention may be used in a variety of different manners. One manner of using microneedle arrays of the present invention is in methods involving the penetration of skin to deliver medicaments or other substances and/or extract blood or tissue. As discussed above, it may be desired that the height of the microneedles in the microneedle arrays be sufficient to penetrate the stratum corneum.

Microneedle Array Delivery

In addition to having a sufficient length, it may be preferred to provide the microneedle arrays in combination with devices that are capable of delivering the microneedle arrays to a skin impact site in a manner that results in effective piercing of the stratum corneum by the microneedles on the array. Delivery of a microneedle array in accordance with the methods of the present invention will involve application of an impact force to the microneedle array over a short period of time (typically less than about 1 second) such that the microneedles of the array are driven through the stratum corneum at the skin impact site. Application of the impact force may rapidly accelerate the microneedle arrays of the present invention such that impact delivery of the microneedle array with the skin is achieved.

It should be understood that impact delivery of microneedle arrays as discussed herein may not necessarily be limited to microneedle arrays that include microneedles with channels as described above in connection with FIGS. 1–6. The impact delivery devices and methods described herein may be used with many different microneedle arrays.

Figure 7:
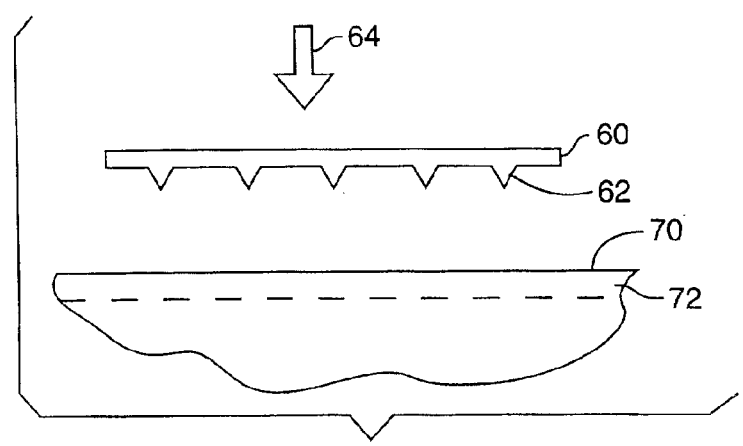
FIG. 7 depicts use of a microneedle array in a manner according to the present invention.
Figure 8:
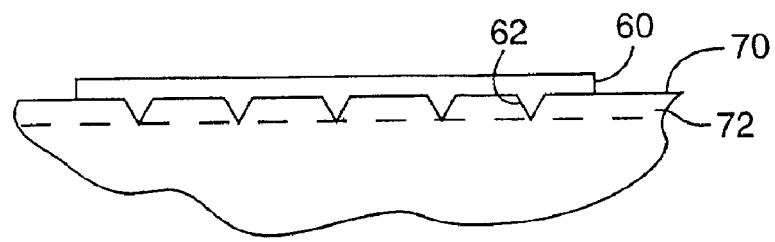
FIG. 8 depicts contact between the microneedle array and skin as depicted in FIG. 7.

Referring to FIG. 7, one method of forcing a microneedle array 60 including microneedles 62 is depicted, with the microneedle array 60 being forced against the skin 70 (with stratum corneum 72) by an impact force 64. FIG. 8 depicts the microneedle array 60 in contact with the skin 70, such that the microneedles 62 penetrate the stratum corneum 72.

The impact force magnitude and duration period are selected to provide effective penetration of the stratum corneum by the microneedles. It may be preferred that the period of time over which the impact force is applied be less than about 500 milliseconds, in some instances, the period may preferably be about 300 milliseconds or less.

The impact force may be applied in a variety of manners. For example, the microneedle array 60 may be positioned a distance from the skin impact site, such that application of the impact force 64 results in acceleration of the microneedle array 60 towards the skin impact site until the microneedle array contacts the skin impact site. In another example, the microneedle array may be positioned in contact with the skin impact site before the impact force is applied to the microneedle array, such that application of the force does not result in acceleration as would be achieved if the microneedle array is positioned away from the skin.

After application of the impact force and subsequent driving of the microneedles through the stratum corneum, it may be desired to remove the microneedle array from contact with the skin impact site within about 1 second or less. In other instances, it may be desirable to retain the microneedle array in contact with the skin impact site for a longer period of time, e.g., about 2 seconds or more.

The maximum magnitude of the impact force may preferably be limited to, e.g., control the pain associated with impact delivery of microneedles arrays in connection with the present invention. For example, it may be preferred to provide impact delivery of the microneedle arrays of the present invention with a maximum impact force about 40 $N/cm^2$ or less, more preferably about 20 $N/cm^2$.

At the other end of the force spectrum, the minimum impact force may vary depending on a variety of factors such as the size of the microneedle array, the size and/or shape of the microneedles, etc.

Figure 9:
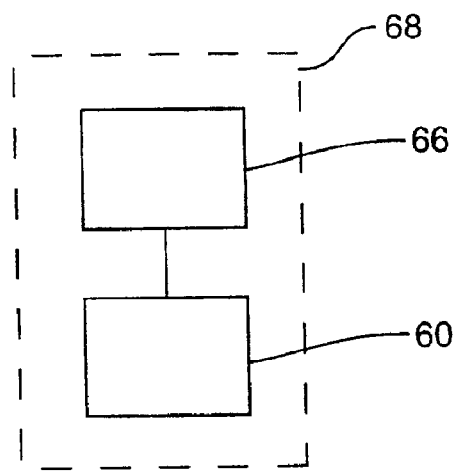
FIG. 9 is a schematic diagram of one device for delivering microneedle arrays in accordance with methods of the present invention.

A wide variety of devices may be used to provide the desired impact delivery of microneedle arrays with the skin of a subject. One such device 68 is illustrated schematically in FIG. 9 as including a microneedle array 60 and a driver 66. The device 68 may be a single-use disposable design, it may be designed for using a single microneedle array 60, or it may be designed to use multiple different microneedles arrays 60.

The driver 66 may be provided by any mechanism capable of applying the desired impact force needed to drive the microneedles into the stratum corneum as discussed above. The driver 66 may be in the form of any device capable of releasing stored energy in the form of the impact force over the durations discussed above, i.e., over a period of less than about 1 second. For example, the driver 66 may include a mechanical spring (e.g., a coil spring, leaf spring, etc.), compressed resilient member (e.g., rubber, etc.), compressed fluids (e.g., air, liquids, etc.), piezoelectric structure, electromagnetic structure, hammer device, etc.

One example of a potentially suitable device 68 may include a lancet driver incorporating a mechanical spring which may be modified, if needed, to provide the desired force to the microneedle array. Typically, a lancet driver may also require some modifications to ensure that the microneedle array is forced against the skin in a manner such that substantially all of the microneedles contact the skin.

Following impact delivery of a microneedle array according to the present invention, it may be desirable to provide vacuum over the surface of the skin impacted by the microneedle array. Application of vacuum to the impact site can be used to extract blood or fluid from the skin penetrated by the microneedles.

Figure 10:
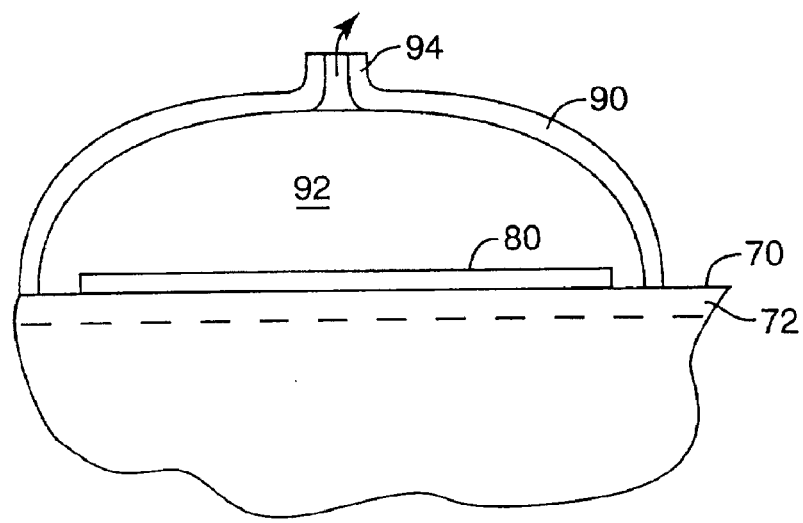
FIG. 10 depicts application of vacuum in connection with methods of the present invention.

Referring to FIG. 10, a vacuum cup 90 is depicted over the skin impact site as depicted in, e.g., FIG. 8. The vacuum cup 90 may preferably include a port 94 that allows for evacuation of the volume 92 defined by the vacuum cup 90. As used in connection with the present invention, "vacuum" is defined as a pressure below the ambient atmospheric pressure surrounding the vacuum cup. The vacuum may be provided by any suitable source, e.g., a pump, syringe, etc.

The microneedles driven into the stratum corneum at the skin delivery site may provide fluid pathways through the stratum corneum. A vacuum applied over the skin delivery site after the microneedles have been driven into the stratum corneum may enhance the passage of fluids through the stratum corneum within the skin delivery site.

The ability of the vacuum drawn within volume 92 to draw fluids through the skin in the skin impact site may be used for a variety of purposes. For example, an indicator 80 capable of detecting the presence or absence of substances or materials in fluids drawn out from the skin impact site may be located on the skin impact site. The indicator 80 may be placed in contact with the skin delivery site before drawing the vacuum over that site or after drawing the vacuum over the skin impact site.

For example, a blood glucose monitoring strip 80 may be placed over the skin impact site with the fluid drawn through the impact site activating the strip to provide a glucose reading. In such a method, sufficient fluid may be drawn under, e.g., conditions of 0.5 atm of vacuum for less than 1 minute.

In addition to indicators for determining blood-glucose levels, the device and methods of the present invention may be used to extract fluid for other indicators such as those capable of determining the presence, absence or amounts of a variety of materials in fluids (e.g., blood) such as dissolved oxygen, carbon dioxide, lactic acid, illicit drugs, etc.

Additionally, the demonstration of effective penetration of the stratum corneum may provide a useful pathway for localized, painless administration of pharmaceuticals. Topically applied pharmaceuticals may be more effectively delivered through the skin after penetration of the stratum corneum by the microneedle arrays of the present invention. In other variations, the microneedle array penetration may be coupled with an electrical or ultrasonic device to deliver larger drugs through the skin more rapidly that is possible through uncompromised tissue.

Where used for the delivery of medicaments or other substances (or the removal of fluids), it may be desirable to include one or more reservoirs in fluid communication with the conduit structures formed in the microneedle arrays. Examples of such reservoirs may be described in, e.g., U.S. Pat. No. 3,964,482 (Gerstel et al.). The reservoirs may be in fluid communication with the conduit structures on the front side of the microneedle arrays (i.e., the side from which the microneedles project) or they may be in fluid communication with the conduit structure from the back side (i.e., the side opposite the front side) through vias or other fluid pathways.

All patents, patent applications, and publications cited herein are each incorporated herein by reference in their entirety, as if individually incorporated by reference. Various modifications and alterations of this invention will become apparent to those skilled in the art without departing from the scope of this invention, and it should be understood that this invention is not to be unduly limited to the illustrative embodiments set forth herein.

What is claimed is:

1. A microneedle array device comprising:
    a plurality of microneedles projecting from a substrate surface, wherein each of the microneedles comprises a tapered shape comprising an outer surface, a base proximate the substrate surface, and a tip distal from the base, and further wherein the base is elongated along an elongation axis on the substrate surface such that the base comprises opposing ends along the elongation axis;
    a channel formed in the outer surface of each microneedle of the plurality of microneedles, each channel extending from the base towards the tip of the microneedle, wherein the channel terminates short of the tip of the microneedle; and
    a conduit structure formed on the substrate surface, the channel in each microneedle of the plurality of microneedles is in fluid communication with the conduit structure on the substrate surface.

2. A device according to claim 1, wherein the channel extends from one of the opposing ends of the elongated base towards the tip of the microneedle.

3. A device according to claim 1, wherein the channel extends from an intermediate location between the opposing ends of the elongated base towards the tip of the microneedle.

4. A device according to claim 1, wherein the base comprises an oval.

5. A device according to claim 1, wherein the channel comprises a channel depth, and further wherein the channel depth at the base of the microneedle is less than half of the dimension of the base as measured between the opposing ends.

6. A device according to claim 1, wherein the elongation axes of the plurality of microneedles are aligned with each other on the substrate surface.

7. A device according to claim 1, wherein the conduit structure comprises a series of barriers projecting from the substrate surface, with fluid pathways of the conduit structure being defined by the barriers.

8. A microneedle array device comprising:
    a plurality of microneedles projecting from a substrate surface, wherein each of the microneedles comprises a tapered shape comprising an outer surface, a base proximate the substrate surface and a tip distal from the base;
    a channel formed in the outer surface of each microneedle of the plurality of microneedles, each channel extending from the base of the microneedle towards the tip of the microneedle, wherein the channel terminates short of the tip of the microneedle; and a conduit structure formed on the substrate surface, the channel in each microneedle of the plurality of microneedles is in fluid communication with the conduit structure on the substrate surface.

9. A device according to claim 8, wherein, for each microneedle of the plurality of microneedles, the base of the microneedle is elongated along an elongation axis on the substrate surface such that the base comprises opposing ends along the elongation axis, and wherein the channel extends from one of the opposing ends of the elongated base towards the tip of the microneedle.

10. A device according to claim 9, wherein the elongation axes of the plurality of microneedles are aligned with each other on the substrate surface.

11. A device according to claim 8, wherein, for each microneedle of the plurality of microneedles, the base of the microneedle is elongated along an elongation axis on the substrate surface such that the base comprises opposing ends along the elongation axis, and wherein the channel extends from an intermediate location between the opposing ends of the elongated base towards the tip of the microneedle.

12. A device according to claim 11, wherein the elongation axes of the plurality of microneedles are aligned with each other on the substrate surface.

13. A device according to claim 8, wherein the base comprises an oval.

14. A device according to claim 8, wherein the channel comprises a channel depth, and further wherein the channel depth at the base of the microneedle is less than half of a maximum dimension of the base on the substrate surface.

15. A device according to claim 8, wherein the conduit structure comprises a series of barriers projecting from the substrate surface, with fluid pathways of the conduit structure being defined by the barriers.

16. A microneedle array device comprising:

a plurality of microneedles projecting from a substrate surface on a substrate, wherein each of the microneedles comprises a tapered shape comprising an outer surface, a base proximate the substrate surface, and a tip distal from the base, and further wherein the base is elongated along an elongation axis on the substrate surface such that the base comprises opposing ends along the elongation axis;

a channel formed in the outer surface of each microneedle of the plurality of microneedles, each channel extending from the base towards the tip of the microneedle, wherein the channel does not extend through the substrate, and wherein the channel terminates short of the tip of the microneedle; and a conduit structure formed on the substrate surface, the channel in each microneedle of the plurality of microneedles is in fluid communication with the conduit structure on the substrate surface.

17. A device according to claim 16, wherein the channel extends from one of the opposing ends of the elongated base towards the tip of the microneedle.

18. A device according to claim 16, wherein the channel extends from an intermediate location between the opposing ends of the elongated base towards the tip of the microneedle.

19. A device according to claim 16, wherein the base comprises an oval.

20. A device according to claim 16, wherein the channel comprises a channel depth, and further wherein the channel depth at the base of the microneedle is less than half of the dimension of the base as measured between the opposing ends.

21. A device according to claim 16, wherein the elongation axes of the plurality of microneedles are aligned with each other on the substrate surface.

22. A device according to claim 16, wherein the conduit structure comprises a series of barriers projecting from the substrate surface, with fluid pathways of the conduit structure being defined by the barriers.

23. A microneedle array device comprising:

a plurality of microneedles projecting from a substrate surface on a substrate, wherein each of the microneedles comprises a tapered shape comprising an outer surface, a base proximate the substrate surface and a tip distal from the base;

a channel formed in the outer surface of each microneedle of the plurality of microneedles, each channel extending from the base of the microneedle towards the tip of the microneedle, wherein the channel terminates short of the tip of the microneedle, and wherein the channel does not extend through the substrate; and a conduit structure formed on the substrate surface, the channel in each microneedle of the plurality of microneedles is in fluid communication with the conduit structure on the substrate surface.

24. A device according to claim 23, wherein the base comprises an oval.

25. A device according to claim 23, wherein the channel comprises a channel depth, and further wherein the channel depth at the base of the microneedle is less than half of a maximum dimension of the base on the substrate surface.

26. A device according to claim 23, wherein the conduit structure comprises a series of barriers projecting from the substrate surface, with fluid pathways of the conduit structure being defined by the barriers.

* * * * *

UNITED STATES PATENT AND TRADEMARK OFFICE
CERTIFICATE OF CORRECTION

PATENT NO. : 6,881,203 B2 Page 1 of 1
DATED : April 19, 2005
INVENTOR(S) : Delmore, Michael D.

It is certified that error appears in the above-identified patent and that said Letters Patent is hereby corrected as shown below:

Title page,
Item [56], References Cited, FOREIGN PATENT DOCUMENTS, add:
-- WO      WO 02/72189     9/2002
  WO      WO 98/00193     1/1998 --.

Signed and Sealed this

Sixth Day of September, 2005

JON W. DUDAS
*Director of the United States Patent and Trademark Office*